(12) United States Patent
Van Den Bossche et al.

(10) Patent No.: US 12,064,375 B2
(45) Date of Patent: Aug. 20, 2024

(54) WHOLE-BODY HYPERTHERMIA SYSTEM

(71) Applicant: ELMEDIX NV, Leuven (BE)

(72) Inventors: Johan Van Den Bossche, Linden (BE); Liesbet Conings, Linden (BE); John-Paul Bogers, Boechout (BE)

(73) Assignee: Elmedix BVBA, Leuven (BE)

( * ) Notice: Subject to any disclaimer, the term of this patent is extended or adjusted under 35 U.S.C. 154(b) by 820 days.

(21) Appl. No.: 17/049,988

(22) PCT Filed: May 2, 2019

(86) PCT No.: PCT/EP2019/061317
§ 371 (c)(1),
(2) Date: Oct. 23, 2020

(87) PCT Pub. No.: WO2019/211411
PCT Pub. Date: Nov. 7, 2019

(65) Prior Publication Data
US 2021/0228406 A1  Jul. 29, 2021

(30) Foreign Application Priority Data
May 2, 2018  (EP) .................................... 18170473

(51) Int. Cl.
*A61F 7/00* (2006.01)
*A61F 7/12* (2006.01)
(Continued)

(52) U.S. Cl.
CPC .......... *A61F 7/0053* (2013.01); *A61F 7/0085* (2013.01); *A61F 7/12* (2013.01);
(Continued)

(58) Field of Classification Search
CPC ........ A61F 7/0053; A61F 7/0085; A61F 7/12; A61F 2007/006; A61F 2007/0093;
(Continued)

(56) References Cited

U.S. PATENT DOCUMENTS 4,691,762 A * 9/1987 Elkins ................ A41D 13/0053
  607/108
5,106,360 A * 4/1992 Ishiwara .............. A61N 5/1002
  600/3

(Continued)

FOREIGN PATENT DOCUMENTS

EP  1581145  4/2004
EP  2401033  9/2010
(Continued)

OTHER PUBLICATIONS

Nikola Cihoric et al., Hyperthermia-related Clinical Trials on Cancer Treatment within the ClinicalTrials.gov Registry, Int J Hyperthemia, 2015; 31(6), pp. 609-614.

(Continued)

*Primary Examiner* — Scott M. Getzow
(74) *Attorney, Agent, or Firm* — BACON&THOMAS,PLLC (57) ABSTRACT

Hyperthermia system for raising the body temperature of the body of an individual to a predetermined target temperature $T_b$ and for stabilizing the body temperature at the target temperature $T_b$, including: a thermally insulated cabinet for receiving the individual, equipped with channeling means to channel fluids into the body of the individual; at least one thermal device to raise the body temperature of the individual, when placed inside said cabinet, and to subsequently maintain the target temperature $T_b$ of the individual; one or more devices for heating fluids to be channeled into the body of the individual via the channeling means; one or more sensors to monitor the temperature and/or heat flux of the individual; and a controller to control the at least one thermal means and the one or more devices for heating fluids. The sensors are connected to the controller to provide temperature values and/or heat flux values.

20 Claims, 1 Drawing Sheet

(51) Int. Cl.
*G16H 20/30* (2018.01)
*A61M 16/10* (2006.01)

(52) U.S. Cl.
CPC ........ *G16H 20/30* (2018.01); *A61F 2007/006* (2013.01); *A61F 2007/0093* (2013.01); *A61F 2007/0096* (2013.01); *A61F 2007/126* (2013.01); *A61M 16/1075* (2013.01)

(58) Field of Classification Search
CPC ....... A61F 2007/0096; A61F 2007/126; G16H 20/30; A61M 16/1075; A61M 2230/205; A61M 2230/40; A61M 1/369; A61M 2205/3368; A61M 2230/04; A61M 2230/202; A61M 2230/207; A61M 2230/50

See application file for complete search history.

(56) References Cited

U.S. PATENT DOCUMENTS

| | | | | |
|---|---|---|---|---|
| 5,578,230 | A * | 11/1996 | Eldon | A47G 9/0215 |
| | | | | 392/383 |
| 6,156,007 | A | 12/2000 | Ash | |
| 6,579,496 | B1 | 6/2003 | Fausset et al. | |
| 2010/0017953 | A1* | 1/2010 | O'Keeffe | A61H 33/06 |
| | | | | 219/480 |
| 2014/0364777 | A1* | 12/2014 | Swyer | A61F 7/0053 |
| | | | | 607/107 |
| 2016/0135987 | A1* | 5/2016 | Mignot | A61F 7/12 |
| | | | | 607/105 |
| 2018/0117249 | A1* | 5/2018 | Pennington | A61B 5/14532 |
| 2019/0083298 | A1* | 3/2019 | Starkweather | A61B 18/0218 |

FOREIGN PATENT DOCUMENTS

| | | |
|---|---|---|
| EP | 2284413 A1 | 2/2011 |
| EP | 2288413 B1 | 3/2012 |
| EP | 3372204 A1 | 9/2018 |
| JP | H1033626 A | 2/1998 |
| WO | 2018078188 A1 | 5/2018 |

OTHER PUBLICATIONS

Yoshihito Kurazumi et al., Convective Heat Transfer Coefficients of the Human Body under Forced Convection from Ceiling, J. Ergonomics 2014, 4:1, pp. 1-6.

J. van der Zee, Heating the Patient: a Promising Approach, Annals of Oncology 13: 2002, pp. 1173-1184.

Nina Worel et al., Hepatic Dysfunction Contributes to Coagulation Disturbances in Patients Undergoing Whole Body Hyperthermia by use of Extracorporeal Circulation, Int J Artif Organs 2014; 37(00); pp. 1-12.

European Search Report in corresponding European Application No. 18170473.5 dated Oct. 18, 2018.

International Preliminary Report on Patentability in corresponding PCT Application No. PCT/EP2019/061317, dated May 8, 2020.

International Search Report and Written Opinion in corresponding PCT/EP2019/061317, dated Aug. 5, 2019.

Second Written Opinion in corresponding PCT/EP2019/061317, dated Mar. 17, 2020.

International Preliminary Report on Patentability in corresponding PCT/EP2019/061317, dated May 29, 2020.

* cited by examiner

WHOLE-BODY HYPERTHERMIA SYSTEM

TECHNICAL FIELD

The present invention relates to a whole-body hyperthermia system for raising the body temperature of an individual to a predetermined target temperature $T_b$ and for stabilizing the body temperature at the target temperature $T_b$. The present invention further relates to a method for subjecting a patient to a whole-body hyperthermia condition and to an anti-tumor compound for use in the treatment of e.g. cancer.

BACKGROUND

Known cancer therapies, such as surgery, irradiation, and chemotherapy, aim to maximally remove tumor tissue while preserving healthy tissue as much as possible. However, surgery and irradiation are applied locally, and small amounts of cancer cells which are at remote positions from the site of intervention may remain undetected and may not be removed. Equally, chemotherapy often does not kill all tumor cells.

Consequently, improved or alternative anti-tumor therapies are needed.

It has been described that tumor cells are sensitive to stress conditions, such as elevated temperatures. Indeed, treatment at temperatures between 40° C. and 44° C. is cytotoxic for cells in an environment with a low PO2 and low pH, conditions that are found specifically within tumor tissue, due to insufficient blood perfusion. Under such conditions, radiotherapy is less effective and systemically applied cytotoxic agents will reach such areas in lower concentrations than in well perfused areas. Therefore, the addition of hyperthermia to radiotherapy or chemotherapy will result in at least an additive effect. Furthermore, the effects of both radiotherapy and many drugs are enhanced at an increased temperature.

Hyperthermia can be induced locally (by external or internal energy sources), regionally (by perfusion of organs or limbs, or by irrigation of body cavities), or over the whole body [reviewed in van der Zee (2002) *Ann. Oncol.* 13, 1173-1184; Heating the patient: a promising approach?].

Cihoric N et al. (2015) *Int J Hyperthermia* 31, 609-614 "Hyperthermia-related clinical trials on cancer treatment within the ClinicalTrials.gov registry." gives an overview of 109 clinical trials in which hyperthermia was part of the treatment regimen. 12 of these were performed with whole-body hyperthermia. Devices and methods to apply local hyperthermia have been described in EP2401033, EP2401033, EP2284413, EP1581145.

Worel et al. (2014) *Int. J. Artif. Organs.* 37, 1-12 describe methods and devices to apply whole-body hyperthermia on cancer patients under moderate sedation allowing spontaneous breathing.

Japanese patent application publication no. JP H10-33626 describes an apparatus for the treatment of cancer and AIDS, by use of whole-body hyperthermia. U.S. Pat. No. 6,579,496 describes a method for hyperthermia, including extracorporeal blood heating and sorbent-based detoxification. U.S. Pat. No. 6,156,007 discloses an apparatus for whole-body hyperthermia including a dialyzer.

Elevated temperatures, mimicking severe near-lethal fever, are difficult to apply in a "whole-body" approach, especially for prolonged periods (e.g. more than 6 hours). This is in part due to the fact that it is difficult to obtain a homogenous, or uniform, and accurately maintained elevated temperature of treatment in the body, due to inter alia the influence of the body's own metabolism, which will tend to raise the temperature of certain organs more than others. There is the additional complication that specific body parts may have to be maintained at a lower temperature than the treatment temperature in order to prevent functional damage to the body part.

Methods and devices allowing a long-term whole-body hyperthermia with maximal safety, minimal discomfort, and high clinical efficacy are lacking.

Outside the field of hyperthermic medical treatments, the convective heat transfer coefficient of the whole seated body during forced convection by downward flow from the ceiling has been studied. Kurazumi, Y., Rezgals, L., & Melikov, A. K. (2014). Convective Heat Transfer Coefficients of the Human Body under Forced Convection from Ceiling. *Journal of Ergonomics*, 4(1), [1000126]

SUMMARY OF THE INVENTION

According to an aspect of the present invention, there is provided a whole-body hyperthermia system for raising the body temperature of the entire body of an individual to a predetermined target temperature $T_b$ and for stabilizing said body temperature at said target temperature $T_b$, said system comprising:
- a thermally insulated cabinet for receiving said individual, equipped with channeling means to channel fluids into the body of said individual;
- at least one thermal means, configured to raise said body temperature of said individual, when placed inside said cabinet, and to subsequently maintain the target temperature $T_b$ of said individual;
- one or more devices for heating fluids to be channeled into the body of said individual via said channeling means;
- one or more sensors configured to monitor the temperature and/or heat flux of said individual, when placed inside said cabinet; and
- a controller configured to control said at least one thermal means and said one or more devices for heating fluids;

wherein said one or more sensors are connected to said controller so as to provide monitored temperature values and/or said monitored heat flux values to said controller; and wherein said at least one thermal means comprises means for heating air and injecting said heated air into said cabinet so as to impact on the body of said individual.

For the purpose of the present description, the term "cabinet" refers to a confined space in which the patient may be located for the hyperthermia treatment. The cabinet may be a sarcophagus-shaped space, a chest, a box, a chamber, or the like. Alternatively, it may be formed of panels, preferably, from a fabric with heat-isolating properties, which may further take the form of a tent, surrounding the patient. Typically, the cabinet refers to the room, or a heat-sealed, confined part of a room, wherein the patient is located during treatment. When the patient is placed in a bath with fluid, use is made of a larger cabinet for harboring the bath. The cabinet is provided with thermal insulation to prevent the outflow of heat from the cabinet. Said thermal insulation has thus the purpose of reducing heat losses and heat fluxes from the body to its surroundings, as well as from the cabinet to its surroundings to a minimum, ideally to zero. Under these conditions, no thermal energy escapes from the body. As such, the cabinet has the purpose of maintaining an individual at an elevated temperature.

In view of the requirement to inject heated air into said cabinet, the cabinet must be able to evacuate excess air to avoid overpressure. To this end, part or all of the cabinet may be permeable to air or the cabinet may be provided with one or more vents in the form of orifices or valves.

For the purpose of the present description, the term "channeling means" refers to an ensemble of channels, tubes, circuits, through-holes, etc., as required to channel fluids (i.e., liquids or gases) into and out of the patient, when placed inside the cabinet. These may include passive tubing as well as channels that perform additional functions (pumping, heating, cooling, filtering, etc.).

The system of the present invention and the methods based on its application, have the advantage that whole-body hyperthermia can be applied in a more accurate and more homogenous way, thus allowing for a safe application of the treatment over much longer time periods than used in the prior art.

Prior-art methods are applied on patients for short periods only, because of the discomfort of the patient, who is at most moderately sedated. The methods and devices of the present invention allow to compensate for the discomfort that occurs when the whole-body temperature elevation is applied for more than 4 h, more than 6 h, or more than 12 h.

In-vitro research has shown that (tumor) cell damage increases rapidly when the heat treatment is maintained for more than 4 h, even more when it is maintained for more than 6 h, and even more when it is maintained for more than 12 h. The present invention has the advantage that tumor cells can be challenged for a much longer time and that tumor cells death therefore occurs more efficiently compared to shorter treatments.

Use of the system of the present invention for prolonged hyperthermia therapy avoids the selection of heat-resistant tumor cells as may occur with repetitive exposure to hyperthermic conditions for shorter time periods. Indeed, suboptimal conditions as used in the prior art may select those cells with superior heat shock protein repair systems, making the cells resistant to further hyperthermic conditions. With the methods of the present invention, the risk of selecting heat resistant cells is dramatically reduced.

This consequently allows repeating long-term hyperthermic treatments, especially in combination with chemotherapy or other cancer treatments such as but not limited to immunotherapy, gene therapy, molecular therapy, radiation or proton therapy, and the like. Indeed, high temperatures improve the uptake of anti-cancer drugs allowing the use of lower doses of medicaments, and consequently fewer side effects.

The methods of the present invention allow repetitive treatments of long-term hyperthermia combined with the cited therapies at reduced dosages. In combination treatments, the chemotherapeutic compounds can be applied before, during or after the hyperthermia treatment.

Compared to known hyperthermia approaches, the present invention provides improved safety because it provides better homogeneity and accuracy, which in turn allows longer treatment times without causing damage or discomfort to the patient, thus improving clinical efficacy.

Embodiments of the present invention have the advantage that heat loss from the body is reduced and kept to its minimum. When extracorporeal heating devices are used, the temperature at the heating device can be kept close to the target temperature to be achieved at the body. Prior-art methods and devices in which an individual is wrapped in a blanket lose substantial heat via the skin, or via breathing, whereby the heating devices of the patient have to compensate the heat loss by heating the blood to temperatures above the target temperature of the body.

The devices for heating fluids and the thermal insulation of the cabinet cooperate to minimize the loss of heat from the body. This has the advantage that the excess of heat that has to be applied to the body to maintain the target temperature is as low as possible. This in contrast with the prior-art systems with extracorporeal blood heating, in which the blood needs to be heated to substantially higher temperatures than the target temperature to compensate for loss of heat (by respiration, inadequate isolation of the body, etc.), which comes at the risk of damaging blood cells if the hyperthermia is maintained for longer periods.

At the end of a treatment, the thermally insulating function of the cabinet can advantageously at least partially be removed or countered, e.g. by creating a current of cooler air, in order to cool the body's temperature.

The air in the cabinet, surrounding the patient, is in other words fully controlled, in terms of temperature, but also in terms of humidity. Indeed, the cabinet is preferably provided with means for creating an environment at a desired temperature and humidity, with the aim of preventing dehydration of the patient.

Herein, the devices for heating fluids are typically devices for heating air and/or oxygen for respiration, or devices for heating liquids being introduced in the body. Preferably, such devices further also administer said heated air and/or oxygen, or heated liquids to the body.

It is an advantage of such devices heating air and/or oxygen for respiration, that the heat-exchange capabilities of the lungs can be used. The inventors have found that the temperature at which air and/or oxygen for respiration is administered, has a significant influence of the uniformity and safety of heating the body and can substantively support the hyperthermia treatment. Typically, in order to use the lungs for the exchange of heat, the patient is brought under general anesthesia.

Advantageously, the air and/or oxygen that is heated, and administered to the body, has a humidity level that is in service of preventing dehydration of the body. Preferably, an inhalation mask is used to provide the lungs with heated and humidified air (0-100%). This allows to apply a different temperature to the lungs compared with the rest of the body.

For the purpose of the present invention, the term "at least one thermal means" refers to means that are configured to provide a fast heating and maintain the target temperature.

In an embodiment of the system according to the present invention, the means for heating air and injecting said heated air are configured to inject the heated air at an air velocity of at least 0.3 m/s, preferably at least 0.5 m/s, most preferably at least 1 m/s.

The inventors have found that air velocities above the listed thresholds provide better heat exchange, and are therefore better adapted to bringing the patient to the target hyperthermic temperature and keeping him or her there, than slower air velocities.

In an embodiment of the system according to the present invention, said at least one thermal means further comprises means for humidifying said air to be injected into said cabinet.

The inventors have found that humidification of the air prior to insertion into the cabinet not only avoids drying out the patient's skin during the hyperthermia therapy, but also improves the heat exchange.

In an embodiment of the system according to the present invention, the devices for heating fluids to be channeled into the body of said individual comprise devices for heating air and/or oxygen for respiration, and/or devices for heating liquids being introduced in the body.

It is an advantage of this embodiment that heat loss through respiration and other fluid exchanges can be minimized or avoided, thus making it easier to keep the patient at the target temperature.

In an embodiment of the system according to the present invention, the sensor monitoring the temperature of the individual comprises one or more of: sensors measuring the temperature internally, sensors measuring the temperature externally and contacting the skin, and sensors measuring the temperature externally and not contacting the skin.

In particular, the means for monitoring the body temperature may be a heat sensitive camera measuring the temperature of a part of the skin of the body. The means for monitoring the body temperature may comprise at least one temperature probe for monitoring at least one temperature signal at at least one location on or within the individual; and means for deriving an overall value, being the monitored body temperature $T_m$, from the at least one temperature signal. Temperature probes for monitoring a temperature signal at a location within the individual may in particular be applied at or near a particularly heat-sensitive organ such as the liver, the kidneys, or the colon. The signal from such probes can be used as a shutdown trigger to protect the patient from harmful overheating.

Alternatively or additionally, heat flux sensors may be attached to the skin of the individual.

Preferably, the sensors are interconnected by use of a network, optionally a wireless network, wherein a sensor controller monitors, preferably continuously, the outcome of the individual sensors and steers the heating and/or cooling of the whole body, specific body parts and/or individual organs. It is an advantage of such a network and a controller steering temperature at local level, that hotspots in the body, potentially due to increased exothermic activity of organs, can be avoided.

According to embodiments of the present invention, the system can monitor and control all heat fluxes to and from the body and therefore the temperature of all body parts, using a combination of the sensor measurements and the specifications of the cabinet, the at least one thermal means and the devices for heating fluids.

Preferably, controller uses at least the monitored body temperature $T_m$ for generating a control signal for the at least one thermal means for steering $T_m$ to the target temperature $T_b$. As explained for embodiments hereinabove, the outcome of at least one temperature sensor or probe is used for deriving an overall value, which is used for steering the heating and/or cooling of the whole body, body parts and/or individual organs.

In embodiments of these systems the system is provided with means for maintaining the monitored body temperature $T_m$ within a range of at most 0.5 K from the predetermined target temperature $T_b$.

Typically, said monitored body temperature $T_m$ represents an overall value that is representative for the temperature stage the heated body temperature can be situated in during the treatment. It therefore has the purpose of serving as an indication for the system to further steer heating (or cooling) of the body.

In an embodiment, the system according to the present invention further comprises a heat exchanger for local application, configured for circulating a heating or cooling fluid, and means to bring said heating or cooling fluid to a set temperature $T_f$, wherein $T_f=T_b\pm0.5$ K.

The heat exchanger for local application may be provided on the skin of the individual, nearby the location of the organ, providing heating or cooling through the skin.

Additionally or alternatively, the heat exchanger for local application may be configured for being at least partially inserted inside said body of said individual. In particular the heat exchanger for local application may be an internally heated or cooled catheter. The heat exchanger may also be or comprise a cooled or heated patch, which is applied in direct contact with such organs as may require to be kept at a different temperature, typically by use of minimally invasive, interventional or keyhole surgery. Accordingly, a partly internal patch may be used to keep an internal organ at a slightly different temperature than the temperature applied to the rest of the body. Organs for which such a different, preferably lower temperature may be targeted include the brain, the liver, the kidneys and the colon. The stomach and the intestines may also be prone to overheating in certain circumstances, in particular as a result of exothermic reactions involving partially digested food that may be present inside (if not removed prior the hyperthermia treatment); accordingly, heat exchangers may also be applied to these organs.

By including heat exchangers for local application, the system of the invention provides added safety against overheating of critical organs, which in turn allows longer treatment times without causing damage or discomfort to the patient, thus improving clinical efficacy.

While $T_f=T_b\pm0.5$ K is believed to provide adequate results, other embodiments may generally operate by choosing $T_f$ in a range between $T_b-1.5$ K and $T_b+1.5$ K, or more preferably in a range between $T_b-1.0$ K and $T_b+1.0$ K.

In a particular embodiment of the system according to the present invention, the heat exchanger for local application and at least one of said one or more sensors configured to monitor the temperature and/or heat flux, are provided as a disposable kit. Keeping the body as a whole, and specific body parts in particular, at the desired temperature during the hyperthermia treatment is an essential part of any hyperthermia treatment. Elements that enable the required thermal regulation, such as the at least one of said one or more sensors configured to monitor the temperature and/or heat flux, and in some embodiments the heat exchanger for local application, are therefore essential to embodiments of the present invention. In view of sterility and hygiene requirements, sensors and heat exchangers that make contact with the patient's body may not be suitable for reuse. It is therefore advantageous to provide those elements as a disposable kit for single use, in combination with a fixed reusable infrastructure comprising the cabinet, and preferably the thermal means, fluid heating means, and controller.

Such kits may further comprise inter alia an isolation element for an individual, such as isolation foil or suit for torso or limbs, or a helmet or cap like device for application on the head, as will be further described below.

In an embodiment, the system according to the present invention further comprises means for monitoring vital signs of the individual, such as respiratory activity, cardiac activity, blood parameters, and urine components.

It is an advantage of this embodiment that the treatment of the patient can be modified in response to changing vital signs, thus improving the chances of a successful treatment and reducing the risk of inadvertently causing harm to the patient.

In a particular embodiment, the monitored blood parameters comprise one or more of pH, PO2, PCO2, salts, lactate concentration, blood sugar, hematocrit values, CPK, and dissolved gases.

These specific blood parameters provide particularly useful information about the state of the patient during the treatment.

In a more particular embodiment, the system is further configured to return the patient to normal body temperature upon detection of a generalized lactate increase.

This embodiment is based inter alia on the insight of the inventors that a general increase of the lactate concentration in the patient's blood is indicative of a detrimental reaction to the hyperthermia. This embodiment is further based on the insight of the inventors that by using this parameter as a trigger for aborting the hyperthermia treatment, undesired harm to the patient can be avoided.

In an embodiment, the system according to the present invention further comprises means to administer additional compounds to the individual, such as transfused blood, chemotherapeutic drugs and/or nutritional compounds, such as salt solutions, and wherein said additional compounds are administered at a temperature $T_b$.

It is an advantage of this embodiment that when the hyperthermia treatment is combined with the provision of compounds, the latter compounds do not interfere with the thermal regime imposed by the thermal means.

It must be noted that the system may further comprise means to administer additional compounds to the individual at a temperature different from $T_b$.

The term "chemotherapeutic drugs" is meant to include, without limitation, cytotoxic and cytostatic drugs. It should be noted that the additionally administered compounds may also include other agents, including small molecules and antibodies.

In an embodiment, the system according to the present invention further comprises one or more isolation elements for an individual, such as isolation foil or suit for torso or limbs, or a helmet or cap for application on the head.

As the heat exchange is mainly accomplished by means of injected heated air, shielding specific body parts (such as the head) from the air flow contributes to preventing overheating of such body parts.

In an embodiment, the system according to the present invention further comprises means to modify an orientation or posture of said body, when placed inside said cabinet.

As the patient may be sedated during the treatment, it may not be possible for the patient to change his position of his own motion. It is therefore advantageous to provide means to allow the caretaker to change the patient's position. These means may be mechanized (including pneumatics, pumps, levers, motorized rolls, etc., for example integrated in or positioned under a mattress or support upon which the patient is positioned) or manual (including sleeves reaching into the cabinet, which allow manipulation of the patient from outside the cabinet).

In a particular embodiment, the system is further adapted to activate said means to modify an orientation or posture of said body in response to a detection of an elevated creatine phosphokinase (CPK) level in blood of said individual.

As an increase in detected CPK levels may be indicative of the onset of muscle breakdown due to prolonged compression (in particular as a result of lying in the same position for a prolonged period of time), CPK levels may be used as a trigger to initiate an automated position adjustment, to prevent muscular atrophy.

In embodiments of these systems, the first thermal means comprises a pump selected from the group consisting of a roller pump, a centrifugal pump, a pulsatile pump and a non-occlusive roller pump.

According to an aspect of the present invention, there is provided a method for subjecting an individual to a whole-body hyperthermia condition using a whole-body hyperthermia system as described above, the method comprising the steps of
placing the individual in the cabinet;
activating the at least one thermal means;
monitoring the temperature and/or heat flux of said individual;
deriving from said monitoring an overall value, being the monitored body temperature $T_m$;
generating a control signal from the monitored body temperature $T_m$ for the at least one thermal means, for steering $T_m$ to the target temperature $T_b$;
whereby the individual is kept in a hyperthermia condition for at least 6 hours, or at least 8 hours, or at least 12 hours, during which period the monitored body temperature $T_m$ of the patient does not deviate by more than 0.5 K, or 1.0 K from the predetermined target temperature $T_b$.

In embodiments of these methods, heat losses from the individual are compensated by one or more of the following steps:
heating the skin of the individual or parts thereof by controlling the temperature of the air surrounding the individual;
applying isolation on one or more parts of the body;
heating air used for respiration to a controlled temperature;
heating liquids for administering, nutrients, moisture or medicaments to a controlled temperature.

In embodiments of these methods, the at least one thermal means comprise a first thermal means and a second thermal means which differ from each other. In specific embodiments of these systems the first thermal means has at least a first portion and at least a second portion, wherein the at least first portion of the first thermal means is arranged to raise the body temperature of at least a first series of body parts of the individual to the target temperature $T_b$, and wherein the at least second portion of the first thermal means is arranged to prevent at least a second series of body parts to exceed a target temperature $T_s$, wherein the temperature $T_s$ is lower than the temperature $T_b$.

In embodiments of these methods, the individual is kept in hyperthermia condition at a temperature between 40 and 42° C.

In embodiments of these methods, the individual is kept in hyperthermia condition for at least 12 hours.

In a typical embodiment of these methods, the individual is a cancer patient.

In a typical embodiment of these method, the individual is under complete narcosis.

Another aspect relates to the use of a kit in accordance as described above, in a method as described before.

According to an aspect of the present invention, there is provided an antitumor compound for use in the treatment of cancer, wherein the compound is administered to a patient which is under a whole body hyperthermia of between 41.5° C. and 42.0° C. for at least 6 h.

DETAILED DESCRIPTION OF THE INVENTION

General Aspects

Figure 1:
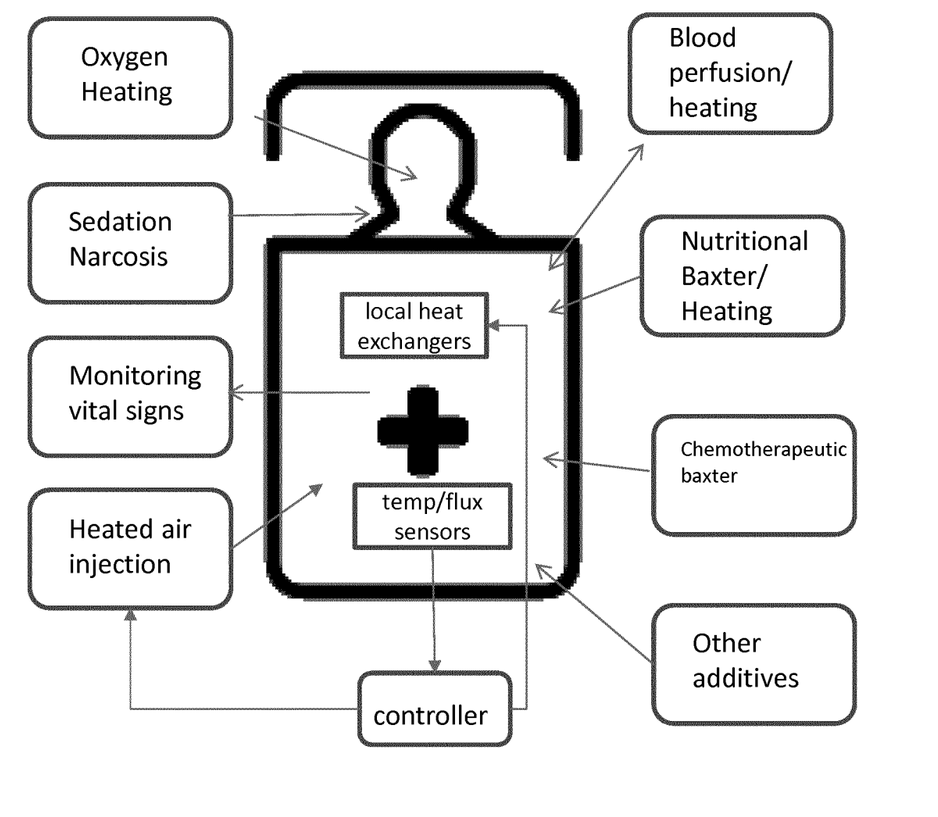
FIG. 1 is a non-limiting schematic illustration of an embodiment of the system according to the present invention.

It is established that the temperature of the human body can be increased up to a temperature of 43° C. for a longer period without serious adverse effects. This insight is the basis for hyperthermia treatments, whereby the therapeutic effect of certain drugs is augmented by locally or globally increasing the body temperature. This effect applies for example to chemotherapeutic agents (including cytotoxic drugs and cytostatics) used to treat cancer, which may be supplied to the patient an intravenous drug, as a topical cream (in particular for skin cancers such as melanoma), or via the injected air (see below). A deliberately induced increase in body temperature is also believed to increase the efficacy of other therapies, such as immunotherapy/gen therapy or molecular therapy.

However, some body parts cannot exceed this temperature without sustaining damage. As a consequence, the target temperature $T_b$ is chosen in the range of 40.5° C. to 43° C., preferably in the range of 41° C. to 42.5° C., more preferably in the range of 41.5° ° C. to 42.0° C. It is further understood that good results can be obtained when $T_b$ is around 41.5° C.

The apparatus of the present invention and the methods of using it envisage that the temperature of the body is raised to a target temperature $T_b$ which is preferably 41° C., 41.5° C., 42° C., 42.5° C. or 43° C. The at least one thermal means may be arranged for raising the patient's body temperature at a rate of at least 1 K/h, preferably at a rate of at least 2 K/h, more preferably at a rate of at least 3 K/h, even more preferably at a rate of at least 4 K/h, more preferably at a rate of at least 5 K/h, even more preferably at a rate of at least 6 K/h and most preferably at a rate of at least 7 K/h. Preferably, the target temperature is achieved within a period of about 15, 30, 45, 60 or 120 minutes, whereupon the patient is kept at the desired target temperature for the desired duration of the treatment.

For the purpose of raising the body temperature, the whole-body hyperthermia system comprises at least one thermal means. The at least one thermal means comprises means for heating air and injecting said heated air into said cabinet so as to impact on the body of said individual.

As mentioned hereinabove, certain thermally vulnerable parts of the human body, such as the brain, cannot be exposed to high temperatures without sustaining damage. As a consequence, the temperature of the brain is preferably kept at 41.8° C. or below, more preferably at around 41.5° C., and even more preferably at around 41° C. Other body parts that cannot be exposed to an elevated overall body temperature include the liver, the kidneys, and the colon.

According to embodiments of the invention, these body parts are kept at a lower temperature in order to avoid damage, the lower temperature being 41.8° C. or below, preferably 41.5° C., and even more preferably 41° C. For some body parts, even lower temperatures, e.g. 40.5° C., may be targeted.

It is understood that temperature control of all body parts at all times is a crucial aspect for hyperthermia treatment, so that upon heating, vulnerable body parts do not exceed a certain threshold temperature. By controlling the temperature of these vulnerable body parts so as to remain at a safe level, the overall hyperthermia treatment can be applied for a longer period of time, thus increasing the clinical efficacy of the treatment.

The cabinet may be divided in two portions, one portion for example containing the head and the other portion containing the rest of the body, allowing to heat the head of the body to a different, lower temperature than the rest of the body. In an alternative configuration, the head may remain outside the cabinet during the treatment, provided that the cabinet is provided with an opening through which the neck can pass According to embodiments, the head or a part thereof can be kept at a desired temperature by enveloping the head or part of it in a helmet, to shield it from the injected heated air or infrared radiation, as the case may be. The helmet may be provided with a cooling liquid or gel, or a gel-containing blanket provided with cooling. In addition, pressure sensors can be provided to measure excess pressure in the skull which is indicative for overheating of the brain and subsequent brain damage, and the pressure sensors may be connected to suitable alarms or controllers that shut down the hyperthermia treatment.

According to embodiments of the present invention, the system is provided with means for turning the patient's body or for moving the patient to a different position, for the purpose of allowing said local heating means to scan principally the whole body of the patient. Said patient may thereby be under sedation, or incapable of moving from his/her own strength. The advantage of said embodiments is that this reduces the intervention of staff or nurses. The cabinet may further be provided with sleeved openings allowing said staff to further manipulate the body, when necessary, to a preferred position.

The means for turning the patient's body as such are known from the state of the art and include systems wherein the patient's body is situated on a sheet between two parallel rollers, with the sheet rolled up on both, wherein the rolling up or the unrolling of the sheet on said parallel rollers influences the patient's body position. Alternatively, said means for turning the patient's body includes the use of a mechanical and/or pneumatic means in a mattress under the patient's body, the selective activation of which influences the position of the patient and allows to move or roll the body in a preferred position.

Thermal Means

Advantageously, the thermal means allow for a rapid, controlled heating of the patient's natural body temperature to a higher temperature. A rapid controlled heating has as an advantage that the overall treatment will take less time. This is both in the economic interest of the healthcare provider as advantageous for the comfort of the patient.

The inventors have found that such a rapid and controlled heating can be achieved by injecting heated (and optionally humidified) air into the cabinet so as to impact the body of the patient at a sufficiently high air velocity. The heated air may be injected at an air velocity of at least 0.3 m/s, preferably at least 0.5 m/s, most preferably at least 1 m/s. The injected air may be directed straight at the patient, or tangentially (grazing the patient's body), or thereinbetween.

In addition to the above, the methods and apparatus of the present invention can provide a highly-localized heating of the body, through additional thermal means. It is understood that the term "highly-localized heating of the body" refers to the heating of a specific target of the body, target area of the body, or part of the body, to a predetermined temperature. It should be noted that even if a hyperthermia treatment is intended to only treat a specific target of the body, it may still be useful to increase the general temperature of the body (to a lesser a degree) in order to provide better control and stability of the temperature of the target area. Likewise, it is possible to provide a whole-body hyperthermia as a starting point for a limited-time treatment of selected body parts at an even higher temperature (e.g. at 43° C. during 1 h).

Melanomas are a typical example of such a localized body target. Other localized tumors (stage 1-3 cancer tumors) may likewise form targets to which highly-localized heating may be applied. For this purpose, said at least one thermal means comprise a local heating means for raising the body temperature of said specific target, target area or body part.

Another example of a localized body target to which the localized heating can be applied, is the peritoneum in the case of treatment of peritoneal mesothelioma. A known therapy for this condition is Heated Intraperitoneal Chemotherapy (HIPEC), which is often combined with cytoreductive surgery. The inventors have found that the accuracy of this treatment can be further increased when used in combination with a whole-body hyperthermic treatment. Indeed, by increasing and accurately controlling the target area, the heated chemotherapeutic drugs are administered in an environment the temperature of which approximates the temperature of the administered drugs. In turn, the temperature of the target area can be better controlled if a whole-body hyperthermia is induced, even if it is at a temperature that remains below the temperature of the target area.

Highly-localized heating may be applied to heat the target of the body, target area of the body or body part, to a temperature which may even exceed, typically for a period of time being no longer than 1 h, the target temperature. It has been found that such heating makes the tissue more responsive to a subsequent treatment such as local ionizing irradiation.

The local heating means may comprise one or more focused infrared radiation means. In a preferred embodiment, the infrared radiation means comprise a two-dimensional scanning arrangement, with at least one movable infrared radiation head, for scanning the body (or a part thereof) and heating the specific target, target areas or body parts of interest. The specific targets, target areas or body parts can be heated to individual temperatures, by controlling the speed at which the at least one infrared radiation head moves over the area of the body and the radiation intensity. It is thereby understood that for a given radiation intensity, a lower speed results in a higher temperature of that area. Preferably, the arrangement is provided with a detector adapted to detect abnormalities, such as melanoma, and to adapt the speed of the at least one infrared radiation head.

Additionally or alternatively, the local heating means may be provided with a patch or a reservoir for application on said target, target area or body part. A fluid brought to a predetermined temperature can be pumped through the reservoir for providing highly-localized heating for said target, target area or body part. Advantageously, the temperature of said fluid can be such that the local temperature of the body can exceed the target temperature which has been determined for the rest of the body. As such, application of said patch or reservoir may be used to locally and temporarily break through a lethal thermal barrier. The reservoir may be provided with an insulating material for thermally insulating at least part of the reservoir from body parts surrounding the target to which the reservoir is applied. Thus, overheating of any organs or parts surrounding the target of local heating can be avoided. Furthermore, said reservoir or patch is preferably provided with a heat flux sensor and/or temperature sensor to provide feedback to the controller.

Additionally or alternatively, the local heating means may be provided with additional heated air injectors.

The temperature of certain body parts or organs cannot exceed specific values, as explained here above, to avoid tissue damage. For example, in order to avoid damage, the temperature of the brain cannot exceed 41.8° C.; therefore, the temperature is preferably 41.5° C., more preferably 41° C. Other organs for which a different, preferably lower temperature may have to be targeted in order to avoid damage to the organs include the liver, the kidneys, the colon, the stomach, and the intestines.

Simply shielding the relevant areas of the body from the injected heated air may not be enough to keep these organs at a lower temperature, because they may receive heat via the heated fluids administered to the patient (see below), and because they may generate heat by the body's own metabolism. Therefore, beside the thermal means configured to heat a first series of body parts of the patient to the target temperature $T_b$, additional thermal means may be provided for preventing a second series of body parts of the patient of exceeding a temperature $T_s$, which is lower than $T_b$. $T_s$ is not higher than 41.8° C., preferably not higher than 41.5° C., more preferably not higher than 41.3° C., and even more preferably not higher than 41° C. and most preferably not higher than 40.5° C. It is however understood that each body part of said second series may have an individual characteristic temperature which may not be exceeded. This may be achieved by using several air injectors located at different points where air at different temperatures is injected, or by using one air injector in combination with additional thermal means that provide localized heating (e.g. radiators, specifically in the infrared spectrum) or cooling (e.g. cold patches).

The brain can for example be cooled by applying a cooling cap, a cooling garment or a cooling pack around the head of the individual. Fluid is preferably circulated in or through the cooling cap, the ingoing fluid having preferably the temperature which is at most the temperature that is targeted for the brain.

Alternatively, means for cooling individual organs may be applied on the surface of the organ itself, typically by use of minimally invasive or keyhole surgery. The organ is then cooled via an inflow/outflow of a cooling liquid through the applied cooling means, which may take the form of a patch. Said means for cooling individual organs is preferably placed in contact with the organ or wrapped at least partially around it with the active cooling side oriented towards the organ itself.

For maintaining the liver below a certain threshold temperature, gas-based anesthesia may be used, resulting in a reduced activity and a slower metabolism of the liver.

Said means for cooling individual organs may in particular be applied to the brain, the liver, the kidneys, the stomach, and/or the intestines. Said means for cooling individual organs may also be applied to other organs.

Hence, by avoiding the more vulnerable body parts of said second series, such as the brain, to exceed the temperature $T_s$, tissue damage of the vulnerable body parts can be avoided, while other body parts, are allowed to be heated to the target temperature $T_b$.

According to certain embodiments, the means for cooling individual organs are controlled by use of an organ based thermal model, having the purpose of continuously monitoring and adjusting the overall temperature of each of said organs individually. It must be noted in this respect that the temperature of organs not only depends on the externally applied heat sources as described above, but also on the influence of the patient's basal metabolism, which generates heat at a rate of approximately 100 W for a human at a body temperature of 37° C., and even more when the body temperature is raised.

Devices for Heating Fluids

The whole-body hyperthermia treatment system according to the present invention further comprises devices for heating fluids, applied in particular to fluid circuits which are at least partially within the patient, wherein a fluid, heated by a heat exchanger to a set temperature $T_f$, is circulated through the fluid circuit.

The temperature $T_f$ is in the range of $T_b +/- 0.5$ K. Preferably, the temperature $T_f$ is equal to $T_b$.

According to one embodiment of the present invention, the fluid circuit is an externally heated fluid circuit, wherein the fluid is the blood of the patient and the patient's blood circulatory system is part of the fluid circuit. Part of the patient's blood is removed from the body, then heated by a heat-exchanger, external to the body, and subsequently returned to the body, where the heated blood is circulated further through the patient's body. This external circuit allows the adjust the oxygen content of the blood. This external circuit can be operated at a relatively high throughput rate.

In a preferred embodiment according to the present invention, the fluid circuit is an internally heated fluid circuit, comprising a catheter wherein a heating fluid is circulated. The catheter is introduced in a blood vessel of the patient's body and a fluid is circulated through the catheter. The catheter further comprises a heat exchanger which is arranged for exchanging heat between the heating fluid and the patient's blood. The heating fluid is heated outside of the body in a heat exchanger. The heating fluid is typically circulated through the fluid by a pumping device.

Typically, the pumping device is a peristaltic pump, for heating during limited time periods. Perfusion pumps are used as an alternative since they cause less physical damage to the blood cells.

Air used for respiration can also be heated. Alternatively, the lung function may be interrupted by long term anesthesia and oxygen supply to the blood may be provided via an external (heated) blood circuit. In the latter case, the respiratory function of the patient should be monitored to detect any attempt at spontaneous breathing by the patient, which would be indicative of the wearing off of the anesthesia.

Once a desired temperature is obtained using the thermal means, the intensity of the thermal means is reduced by the controller, and the focus is on maintaining the temperature constant. As the insulation of the cabinet and the devices for heating fluids substantially counteract heat loss from the patient at this stage, the injection of heated air may typically be stopped or strongly reduced.

Vital Signs Monitoring

In one embodiment according to the present invention, the whole-body hyperthermia system is further provided with means for monitoring the patient's body temperature and/or vital signs. The means for measuring vital signs include means for measuring the respiratory activity, if respiration is maintained, as well means for measuring the cardiac activity of the patient while under hyperthermia treatment.

The temperature of the patient, as well as the vital signs, are monitored using procedures well known in the art. Preferably, the temperature (global body temperature and/or temperature at selected critical organs), the temperature evolution over time (global body temperature and/or temperature at selected critical organs) and vital signs are communicated to the caregiver by means of a user interface which may include text displays, graphical displays, auditory signals, and the like.

In one embodiment, the means for measuring the body temperature of the patient comprise at least one single temperature probe for monitoring at least one single temperature signal at at least one location on or within the patient.

In a preferred embodiment, the means for measuring the body temperature comprise at least two temperature probes. Preferably, at least one means for measuring the body temperature is located on the skin of the patient, thereby measuring the temperature of the skin of the patient, and at least one is located on a body part of the patient, other than the skin.

A further means for measuring the body temperature comprises a heat sensitive camera, which can measure the temperature of a significant surface of the skin.

In a more preferred embodiment according to the present invention, the means for monitoring the patient's body temperature comprise a plurality of temperature probes, which generate a plurality of temperature signals. Preferably, the temperature signals are measured in a continuous mode.

The whole-body hyperthermia system further comprises means for deriving, preferably in a continuous mode, from the at least one temperature signal an overall value, which is the monitored body temperature $T_m$. The measured body temperature $T_m$ equals the one single temperature signal, when only one single temperature probe is used. When at least two temperatures probes are used, the measured body temperature is calculated from the at least two temperature signals.

The monitored body temperature $T_m$ is derived from the at least two temperature signals according to procedures well known in the art.

The monitored body temperature $T_m$ is derived in such a way that the optimal condition for hyperthermia treatment of the patient is considered to be achieved, when $T_m$ is equal or close to the predetermined target temperature $T_b$.

It is hereby understood that the monitored body temperature $T_m$ is considered equal or close to the predetermined target temperature $T_b$, when $T_m$ is within the range of at most 0.5 K, preferably of at most 0.4 K, more preferably of at most 0.3 K, even more preferably of at most 0.2 K and most preferably of most 0.1 K from the predetermined target temperature $T_b$.

It is further advantageous to equip the system with means to monitor one or more of heart rate, heart rhythm (ECG), coronary perfusion pressure, mean systemic filling pressure, mean arterial pressure, and central venous pressure. Monitoring of one or more of these parameters may be of particular importance when a pre-treatment cardiac screening of the patient has revealed pre-existing conditions or risk factors that affect the patient's ability to withstand the hyperthermia treatment.

It is further advantageous to equip the system with means to perform blood analysis. Parameters which can be determined are for example pH, PO2, PCO2, salts (in particular K+ concentrations, Na+ concentrations, and the like), lactate concentration, blood sugar, hematocrit values, and various dissolved gases.

It is further advantageous to equip the system with means to perform an assessment of the liquid balance: in particular, the system may be adapted to intermittently measure the patient's urine production (e.g., every 15 minutes), which is an indication of kidney function and of hydration, and/or to permanently or intermittently weigh the patient. In addition, urine analysis may be performed intermittently; it is notably important to detect any coagulation of proteins present in the urine, which may be indicative of undesired overheating (in particular above 41.8°) C.

Other parameters of interest, which the system is preferably equipped to monitor or analyze, include one or more of: arterial bicarbonate, blood ammonium ($NH_4$) level, liver transaminase (SGOT and SGPT), End-Tidal-$CO_2$ in exhaled air (indicative of the sum of circulation [blood pressure, pulse], ventilation, and metabolism; via a $CO_2$ measurement, acidosis or raised metabolism can be detected and subsequently corrected through adaptation of the ventilation frequency and/or volume).

Temperature Control

The whole-body hyperthermia system comprises a controller. The controller is arranged to use the measured body temperature $T_m$ as an input signal for generating a control signal to steer the at least one thermal means and the devices for heating fluids, allowing thereby $T_m$ to approach $T_b$ and stabilize at this temperature.

The at least one thermal means comprises means for heating air and injecting said heated air. A heater of this kind may be controlled by modifying the temperature of the injected air, the amount of injected air, the injection velocity, the injection direction and the timing of the activation of the heater. Depending on the desired temperature and the present body temperature, it may in principle occur that the air injector is controlled so as to inject air at ambient temperature (i.e. "room temperature" as existing outside the cabinet) or at a temperature below ambient temperature, in which case cooling would be required.

The at least one thermal means may further comprise heat exchangers for local application, which may be controlled by modifying the temperature and the flow rate of the heat exchange medium flowing through the exchanger.

The at least one thermal means may further comprise a heat source arranged to raise the overall temperature inside the cabinet as a whole.

The devices for heating fluids may be controlled by modifying the flow rate (if possible for the particular type of fluid) and temperature.

The controllers typically act via feedback mechanisms using proportional-integral-derivative (PID) regulation to prevent overshooting to undesired and medically unacceptable temperatures.

Each device providing heat to the individual can have its own controller unit. Alternatively, a plurality of controller units or all controller units can be incorporated in one dedicated controller. It is possible to operate one or more of the devices providing heat to the individual at a fixed set-point, while applying variable control to other devices.

The locally applied heat exchangers used to keep specific vital organs below a critical temperature may be controlled exclusively or primarily on the basis of a temperature of heat flux measurement obtained by a sensor placed at or very close to the vital organ in question.

In one embodiment according to the present invention, the whole-body hyperthermia system is arranged to raise the patient's body temperature to the target temperature $T_b$ for at least a period of time $t_p$. The period of time $t_p$ is at least 6 h, typically at least 12 h, preferably at least 14 h, more preferably at least 16 h, even more preferably at least 18 h, more preferably at least 20 h, even more preferably at least 22 h, and most preferably at least 24 h.

The systems and methods of the present invention rely on an interaction of a network of temperature sensors, and a network of heat fluxes sensors for raising and maintaining the hyperthermic conditions in an individual. Controllers receive signals from the various sensors and steer the various devices, via feedback systems.

The main heat flux to the individual is provided via injection of heated air into the cabinet, and bodily fluids are heated to prevent heat loss via those media. In addition, patches and infrared radiators may provide localized thermal flows. Temperature sensors and heat flux sensors provide signals to controllers that can adjust the amount of heat that is transported to the patient via these means. This can be done by adjusting the temperature of the liquids and gases, but can also be achieved by adapting the flow rate of liquids and gasses.

Temperature sensing can be on the body by measuring the temperature within the body or at the outside of the body. Temperature sensing can be remote via heat sensitive cameras. Heat sensing can also be indirect by measuring the temperature of the air in the cabinet surrounding the patient, the temperature of the blood inside the patient (sensed for example by means of fiber optic sensor inserted into a blood vessel via a catheter), the temperature of the blood in an extracorporeal system when it leaves the body, the temperature of exhaled air, the temperature of urine.

The coordinated operation of the elements of the system allow a fast heating of the individual without overshooting and allow to maintain a desired temperature which is accurate over time and homogenous for the entire body and safe.

Sedation and Oxygen Supply

In one embodiment according to the present invention, the whole-body hyperthermia system comprises means for bringing the patient under sedation or under anesthesia.

For the purpose of the invention, the term "sedation" refers to the relaxed state of the patient, with or without loss of consciousness, after the administration of drugs. A patient under sedation can be synonymous for a patient under narcosis or under anesthesia. The means for bringing the patient under sedation or under anesthesia are provided to be supplied to the patient at a temperature $T_b$.

Specific embodiments refer to complete narcosis with no breathing. This has the advantage that heat loss via transpiration or via breathing is avoided.

Hereby the necessary oxygen supply for the body is provided by extracorporeal oxygenation of the blood. This is especially advantageous when blood is heated via an extracorporeal circuit.

In one embodiment according to the present invention, the whole-body hyperthermia system comprises means to supply oxygen to the patient. For the purpose of the invention, the term "oxygen" refers to any oxygen-containing gas that can be administered to a patient under sedation.

The oxygen (or air containing oxygen) may be provided at a temperature and humidity adapted to the needs of the patient. The oxygen supplying means are provided to supply oxygen to the patient at a temperature $T_b$. Advantageously, it has been found that the monitored body temperature $T_m$ reaches the predetermined target temperature $T_b$ at a faster pace. Furthermore, it has been found that supplying oxygen at the temperature $T_b$, allows the monitored body temperature $T_m$ to stabilize in a simple way at or close to $T_b$.

Upon complete narcosis spontaneous breathing stops and oxygen is supplied via a mask. Typically, the temperature of the applied gas is adapted to avoid heat losses by introduction of cold gasses.

When an extracorporeal system is used to heat the blood of an individual, oxygen can be supplied to the blood of the patient, which allows to reduce of replace oxygen supply by a breathing apparatus.

Treatment Aspects

In typical embodiments, the systems and methods of the present invention, the individual is placed in a sarcophagus-like cabinet wherein all heating elements and controllers are outside the cabinet whereby the different liquids and gases are provided to the individual via tubing. Alternatively, one or more heating elements are placed within the cabinet to shorten the distance between heated medium and the patient. This still allows to have parts of the system outside the cabinet. For examples gas bottles with air or oxygen air are placed outside the cabinet. "Cold" gas subsequently enters the cabinet where it is heated close to the individual.

In order to prevent dehydration of the body via the skin the cabinet can contain a sensor to monitor the humidity of the ambient air. The hydration level of the skin can be measured directly, e.g. by using a sensor that measures the elasticity of the skin. Humidity can be adjusted by e.g. evaporating water in the cabinet, or by humidifying the gases (air or oxygen) which enter the cabinet, preferably by pre-humidifying the gases in a mixing chamber. Other additives may be added to the air at this stage, including, as the case may be, aerosol chemotherapeuticals (provided that body parts that may not be brought in contact with these substances are adequately shielded).

Advantageously, it has been found that the whole-body hyperthermia system according to the invention can be used for treating an individual who can benefit from a long term (i.e. at least 6 h) hyperthermia treatment. As explained before, such treatment is beneficial for cancer patients since tumor cells are more sensitive to high temperatures. The inventors have found that by increasing body temperature to a judiciously selected, narrow temperature range, tumor cells are sensitized to a much greater extent than healthy cells, rendering them vulnerable to chemotherapy or ionizing radiation (differential cytotoxicity). The highly accurate system of the present invention thus allows to optimally exploit the differential cytotoxicity phenomenon, while also boosting the effectiveness of the chemotherapeutic drugs or the radiation by the temperature increase itself.

The method is also applicable for the treatment of diseases wherein spontaneous fever would occur under normal circumstances. Accordingly, the method is also applicable to bacterial and viral infections. For example, the method can be used in the treatment of antibiotic resistant bacteria, or of viruses for which no, or no effective antiviral compound have been developed. Likewise, the whole-body hyperthermia can be applied to support any type of treatment that benefits from a reaction of the patient's immune system.

In one embodiment according to the present invention, the whole-body hyperthermia system is further provided with means for administering additional compounds to the individual. Non-limitative examples of the additional compounds include transfused blood, nutritional compounds such as glucose and salt solutions, insulin, etc. Preferably, the means are arranged to administer chemotherapeutic (anti-tumor)compounds. The means for administering additional compounds are arranged so that the additional compounds are administered at a temperature $T_b$.

The whole-body hyperthermia system is also useful for the treatment of collagen vascular diseases such as arthritis and psoriasis and for treating hypothermia.

Furthermore, when the system is used for hyperthermia treatment of cancer patients, it has been unexpectedly found that the rate of the temperature increase of the patient's body influences the annihilation mechanism of malign tumor cells. A fast heating rate promotes tumor cell destruction via cell necrosis, whereas a slower heating rate promotes cell destruction via apoptosis.

Since the hyperthermic conditions strongly decrease the viability of tumor cells, these cells become more susceptible to anticancer drugs or ionizing irradiation, thus allowing the use of lower doses with the same therapeutic effect. Lower doses of drugs or irradiation decrease side effects of these therapies.

Furthermore, the heating of the whole body not only has an effect on the primary tumor, localized in an organ of the body, but also on any circulating cells that may be present in other parts of the body and on metastasis.

In the methods of the present invention, different sensors and different types of tubing are used to maintain and adjust the hyperthermic condition and to monitor and control functioning of the body.

Disposable Kit

To facilitate the operation of the system of the present invention, it is advantageous to provide a kit for single use (hereinafter "disposable kit" or simply "kit"), combining some of the elements of the system. It must be noted that the various components described in this section may also be provided in the system, independently of the kit.

The kit may comprise tubing for a fluid circuit for blood supply to the patient and sensors and wiring to monitor the temperature or heat loss from the patient. A typical fluid circuit for arterial blood supply and venous blood drain, is an access device with 2 separate lumen (cannula) or a double lumen access device also called catheter. The fluid circuit is optionally provided with one or more items selected from the group consisting of: a blood pressure sensor, optical blood sensor, temperature sensor, air bubble monitor, air bubble trap, gas and/or fluid flow meter (e.g. by measuring velocity), gas flow filter, oxygen supply, oxygen saturation meter, heparin and/or other fluid/gas access points, membrane oxygenator, heat exchanger.

Optionally the fluid circuit is isolated against heat loss or blood degradation to prevent exposure to light.

In addition to the fluid circuit for arterial blood supply and venous blood drain, the kit may contain one or more of a temperature sensor, a heat flux sensor, a sensor for measuring respiratory activity, a sensor for measuring cardiac activity.

The fluid circuit may also allow to analyze blood in-line within the fluid circuit or to withdraw blood for analysis.

The disposable kit described above may be provided in a cassette-like (pre-wired) form factor for easy handling and mounting on the device reducing the risk for confusion and/or wrong connections.

Additionally, the disposable kit can be provided with an insulation/isolation foil or suit for the patient. Additionally, the disposable can be provided with a hat-like cover to connect to a cooling device especially to cool the patient's brain.

The kit can further contain further thermal means for cooling a selected part of the individual's body, said selected part being typically an individual organ, such as the liver, the kidneys, or the colon. Said means for cooling an individual organ are typically a disposable means.

In a specific composition, a disposable kit includes (1) a heat exchanger for local application (such as a patch) equipped with one or more temperature sensors and/or heat flux sensors, optionally with its own controller unit, and (2)

one or more disposable temperature sensors with connectors for coupling to the controller of the system.

General Remark

While the invention has been described hereinabove with reference to specific embodiments of a system and specific embodiments of methods and of medicaments, this was done to clarify and not to limit the invention. The skilled person will appreciate that options and features only described with reference to the system also apply to the methods and vice versa.

EXAMPLES

Example 1. In Vitro Model for Optimization of the First Means for Heating

A fibroblast cell line (Normal Human Dermal Fibroblasts (NHDF) and a tumor cell line are incubated in DMEM with fetal calf serum in an incubator with 5% $CO_2$. Suitable cell lines are for example Hela cells, HT-1080 (connective tissue cell line with activated N-ras oncogene), A375 (malignant skin melanoma cell line), and A549 (adenocarcinoma human alveolar basal epithelial cells).

Cells are placed in the incubator at 37° C., whereupon the temperature is raised to 41.5° C. over a time period ranging from 30 minutes to 4 hours. The volume of the medium on the cells is kept to a minimum to avoid delay in the heating.

Cell viability is determined and apoptosis and necrosis of cells is measured.

The experiment allows to determine the effect of a shallow or steep increase of the temperature as achieved by the first means when applied on the body.

Example 2. In Vitro Model for Determining Efficiency and Specificity

The above described cells are incubated for different time periods (4 h, 6 h, 8 h, 12 h, 16 h, 20 h, 24 h, 36 h) at different temperatures (37° ° C., 39° C., 40° C., 40.5° C., 41° C., 41.5° C. and 42°) C.

Cell viability is determined and apoptosis and necrosis of cells is measured.

The experiment allows determining the efficiency of the method (% killed tumor cells) and the specificity (% killed tumor cells versus killed normal cells).

The above system can be further used to mimic conditions in tumor tissue (hypoxia, pH) and to determine the effect on cells which have been irradiated or treated with cancer medicaments.

Example 3. In Vivo Model for Long Term Hyperthermia

Mice with a tumor are placed under anesthetics on a heated plate in a heated cabinet. For small laboratory animals the heat transfer is sufficient enough to provide a whole body hyperthermia without the application of first and second means as described in the specification.

Mice are killed and tumor tissue is examined for cell death.

The animal model allows comparing cell death as obtained in example 2 and in the mouse model using the same time period and the same temperature.

The invention claimed is:

1. A whole-body hyperthermia system for raising the body temperature of the entire body of an individual to a predetermined target temperature $T_b$ and for stabilizing said body temperature at said target temperature $T_b$, said system comprising:
 a thermally insulated cabinet for receiving said individual, equipped with channeling means to channel fluids into the body of said individual;
 at least one first thermal means, configured to raise said body temperature of said individual, when placed inside said cabinet, and to subsequently maintain the target temperature $T_b$ of said individual;
 one or more devices for heating fluids to be channeled into the body of said individual via said channeling means;
 one or more sensors configured to monitor the temperature and/or heat flux of said individual, when placed inside said cabinet; and
 a controller configured to control said at least one first thermal means and said one or more devices for heating fluids;
 wherein said one or more sensors are connected to said controller so as to provide monitored temperature values and/or said monitored heat flux values to said controller;
 wherein said at least one first thermal means comprises means for heating air and injecting said heated air into said cabinet so as to impact on the body of said individual;
 wherein said system further comprises means for monitoring blood parameters, wherein said monitored blood parameters comprise one or more of pH, PO2, PCO2, salts, lactate concentration, blood sugar, hematocrit values, CPK, and dissolved gases; and
 wherein said system further comprises a heat exchanger for local application, configured for circulating a heating or cooling fluid, and means to bring said heating or cooling fluid to a set temperature Tf, wherein $Tf=Tb\pm0.5$ K; and
 wherein said system further comprises a second thermal means for preventing a series of heat-sensitive body parts of the patient from exceeding a temperature Ts that is lower than the predetermined target temperature Tb.

2. The whole-body hyperthermia system according to claim 1, wherein said means for heating air and injecting said heated air are configured to inject said heated air at an air velocity of at least 0.3 m/s.

3. The whole-body hyperthermia system according to claim 2, wherein said air velocity is at least 0.5 m/s.

4. The whole-body hyperthermia system according to claim 3, wherein said air velocity is at least 1 m/s.

5. The whole-body hyperthermia system according to claim 1, wherein said at least one first thermal means further comprises means for humidifying said air to be injected into said cabinet.

6. The whole-body hyperthermia system according to claim 1, wherein the devices for heating fluids to be channeled into the body of said individual comprise devices for heating air and/or oxygen for respiration, and/or devices for heating liquids being introduced in the body.

7. The whole-body hyperthermia system according to claim 1, wherein the sensor monitoring the temperature of the individual comprises one or more of: sensors measuring the temperature internally, sensors measuring the temperature externally and contacting the skin, and sensors measuring the temperature externally and not contacting the skin.

8. He whole-body hyperthermia system according to claim 1, wherein said exchanger is configured for being at least partially inserted inside said body of said individual.

9. The whole-body hyperthermia system according to claim 8, wherein said heat exchanger is an internally heated or cooled catheter.

10. The whole-body hyperthermia system according to claim 1, wherein said heat exchanger for local application and at least one of said one or more sensors configured to monitor the temperature and/or heat flux, are provided as a disposable kit.

11. The whole-body hyperthermia system according to claim 1, further comprising means for monitoring vital signs of the individual.

12. The whole-body hyperthermia system according to claim 11, wherein said vital signs of the individual include respiratory activity, cardiac activity, and/or urine components.

13. The whole-body hyperthermia system according to claim 1, further configured to return the patient to normal body temperature upon detection of a generalized lactate increase.

14. The whole-body hyperthermia system according to claim 1, further comprising means to administer additional compounds to the individual, and wherein said additional compounds are administered at the target temperature Tb.

15. The whole-body hyperthermia system according to claim 14, wherein said additional compounds include transfused blood, chemotherapeutic drugs and/or nutritional compounds.

16. The whole-body hyperthermia system according to claim 15, wherein said nutritional compounds include salt-solutions.

17. The whole-body hyperthermia system according to claim 1, further comprising one or more isolation elements for an individual.

18. The whole-body hyperthermia system according to claim 17, wherein said isolation elements include an isolation foil or suit for torso or limbs, or a helmet or cap for application on the head.

19. The whole-body hyperthermia system according to claim 1, further comprising means to modify an orientation or posture of said body, when placed inside said cabinet.

20. The whole-body hyperthermia system according to claim 19, further adapted to activate said means to modify an orientation or posture of said body in response to a detection of an elevated creatine phosphokinase level in blood of said individual.

* * * * *